(12) United States Patent
Sato

(10) Patent No.: US 9,897,545 B2
(45) Date of Patent: Feb. 20, 2018

(54) FLUORESCENCE AND PHOSPHORESCENCE DETECTION DEVICE, FLUORESCENCE AND PHOSPHORESCENCE DETECTION METHOD, AND PAPER-SHEET PROCESSING DEVICE

(71) Applicant: GLORY LTD., Himeji-shi, Hyogo (JP)

(72) Inventor: Takeshi Sato, Himeji (JP)

(73) Assignee: GLORY LTD., Himeji-shi, Hyogo (JP)

( * ) Notice: Subject to any disclaimer, the term of this patent is extended or adjusted under 35 U.S.C. 154(b) by 0 days.

(21) Appl. No.: 15/045,464

(22) Filed: Feb. 17, 2016

(65) Prior Publication Data

US 2016/0238529 A1  Aug. 18, 2016

(30) Foreign Application Priority Data

Feb. 18, 2015  (JP) ................... 2015-029979

(51) Int. Cl.

| G01N 21/64 | (2006.01) |
| G01N 21/86 | (2006.01) |
| G07D 7/12  | (2016.01) |
| G01J 1/46  | (2006.01) |
| G06Q 10/08 | (2012.01) |

(Continued)

(52) U.S. Cl.
CPC .............. *G01N 21/645* (2013.01); *G01J 1/46* (2013.01); *G01N 21/643* (2013.01);
(Continued)

(58) Field of Classification Search
None
See application file for complete search history.

(56) References Cited

U.S. PATENT DOCUMENTS

| 2004/0031931 A1 | 2/2004 | Müller et al. |
| 2004/0061048 A1 | 4/2004 | Vasic et al. |

(Continued)

FOREIGN PATENT DOCUMENTS

| EP | 2 549 445 A1 | 1/2013 |
| JP | 2000-2659 A | 1/2000 |

(Continued)

OTHER PUBLICATIONS

European Search Report (Application No. 16155816.8) (16 pages—dated May 8, 2016).

*Primary Examiner* — Edwin Gunberg
(74) *Attorney, Agent, or Firm* — Renner, Kenner, Greive, Bobak, Taylor & Weber

(57) ABSTRACT

A fluorescence and phosphorescence detection device includes a fluorescence and phosphorescence sensor, a data acquiring unit, and an emission detection unit. The fluorescence and phosphorescence sensor includes a light source that emits an excitation light of a predetermined wavelength, and a photodetection unit that detects fluorescence emission and phosphorescence emission excited from the paper sheet by the excitation light. The data acquiring unit acquires a time-series waveform of a signal outputted from the fluorescence and phosphorescence sensor in response to the detection of the emission in the photodetection unit. The emission detection unit detects the fluorescence emission from the time-series waveform of a period in which the excitation light is emitted from the light source and detects the phosphorescence emission from an attenuation curve appearing on the time-series waveform of a period in which emission of the excitation light from the light source is stopped.

13 Claims, 8 Drawing Sheets

(51) Int. Cl.
*G07D 7/1205* (2016.01)
*B41M 3/14* (2006.01)
*D21H 21/48* (2006.01)
*B42D 25/29* (2014.01)

(52) U.S. Cl.
CPC ......... *G01N 21/6408* (2013.01); *G01N 21/86* (2013.01); *G06Q 10/0875* (2013.01); *G07D 7/12* (2013.01); *G07D 7/1205* (2017.05); *B41M 3/144* (2013.01); *B42D 25/29* (2014.10); *D21H 21/48* (2013.01); *G01N 2021/6413* (2013.01); *G01N 2021/6421* (2013.01); *G01N 2021/8645* (2013.01); *G01N 2021/8663* (2013.01); *G01N 2201/0621* (2013.01); *G01N 2201/1241* (2013.01)

(56) References Cited

U.S. PATENT DOCUMENTS

| | | |
|---|---|---|
| 2005/0163339 A1 | 7/2005 | Watanabe et al. |
| 2011/0052085 A1 | 3/2011 | Ikari et al. |
| 2012/0217416 A1* | 8/2012 | Decoux ................. G07D 7/121 250/459.1 |
| 2014/0097359 A1 | 4/2014 | Vasic et al. |
| 2016/0098879 A1* | 4/2016 | Fukunaga .............. G07D 7/122 250/458.1 |

FOREIGN PATENT DOCUMENTS

| | | |
|---|---|---|
| WO | 2014/132415 A1 | 9/2014 |
| WO | 2015/045186 A1 | 4/2015 |

* cited by examiner

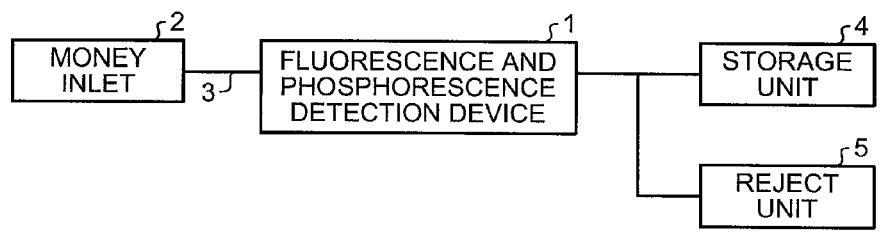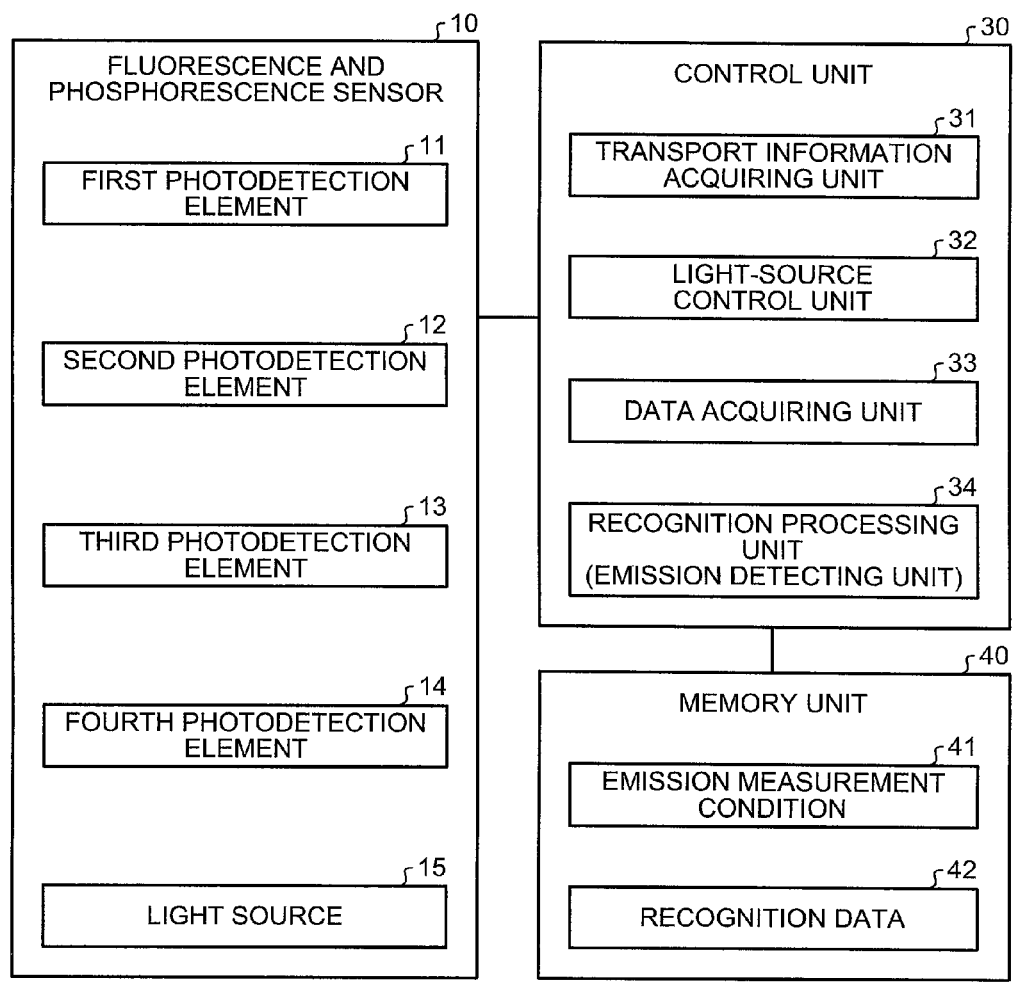

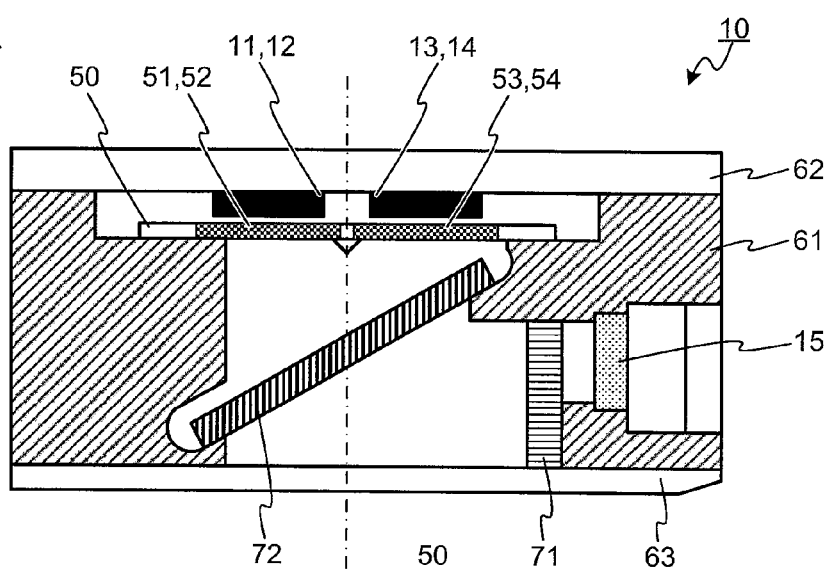
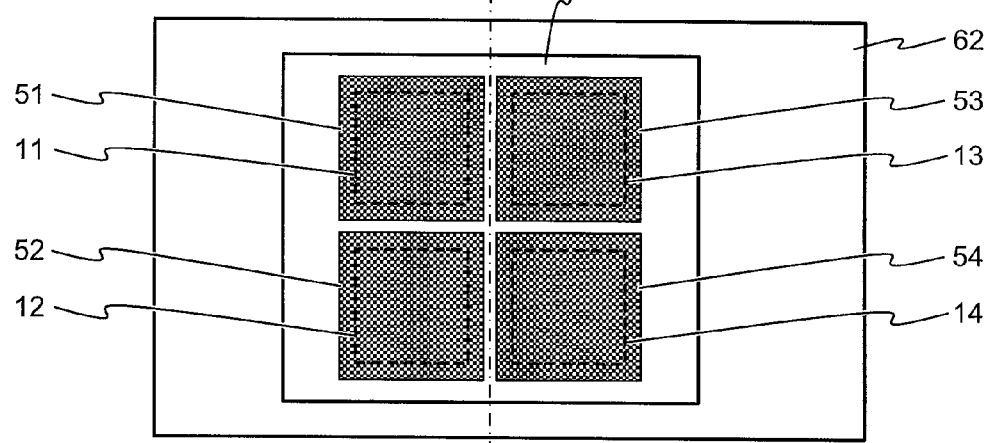

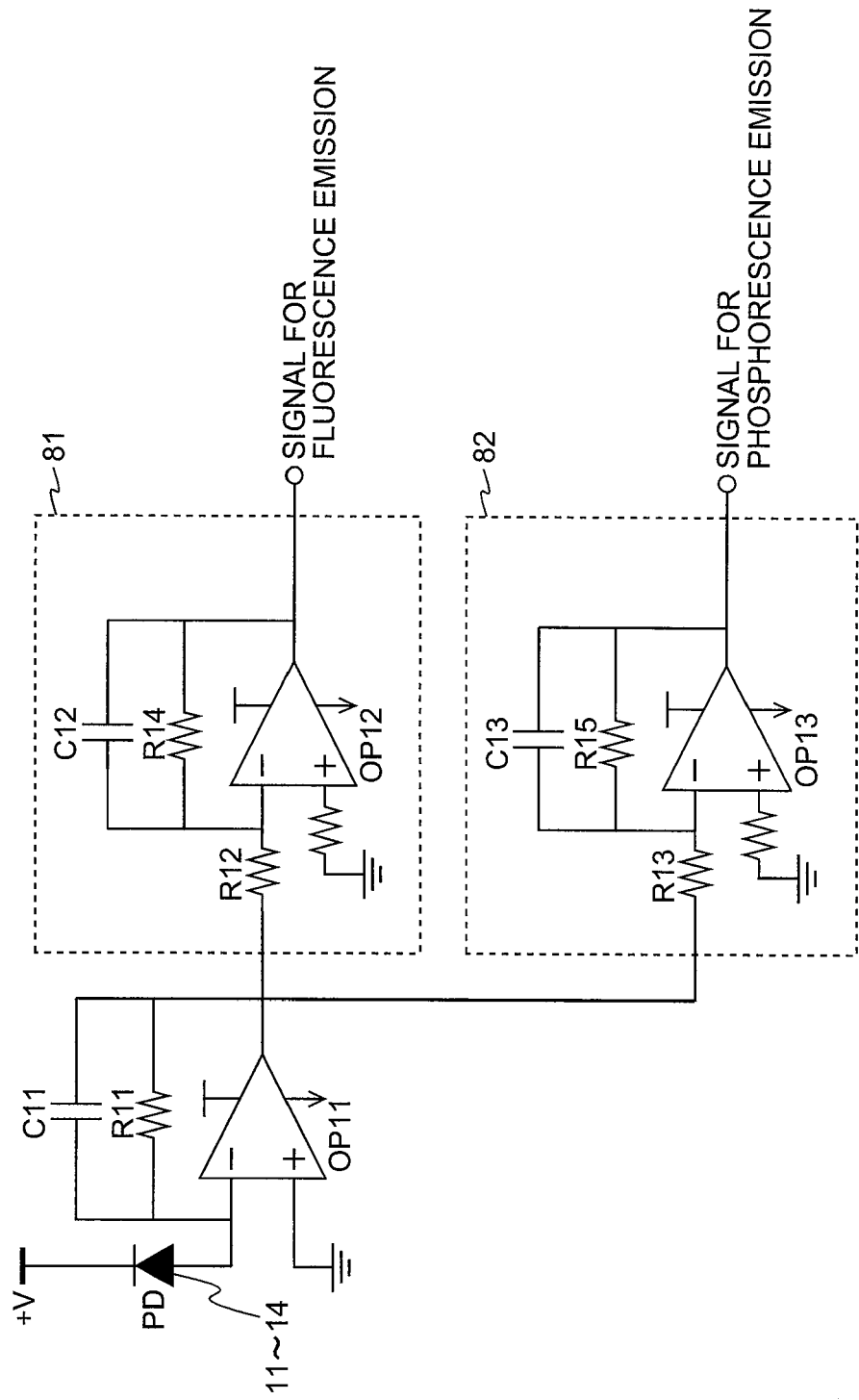

FIG.7A LIGHT SOURCE (UV-LED)

· FIRST PHOTODETECTION ELEMENT
· FIRST FILTER (450~500nm)

· SECOND PHOTODETECTION ELEMENT
· SECOND FILTER (500~550nm)

· THIRD PHOTODETECTION ELEMENT
· THIRD FILTER (550~600nm)

· FOURTH PHOTODETECTION ELEMENT
· FOURTH FILTER (600nm)

FLUORESCENCE AND PHOSPHORESCENCE DETECTION DEVICE, FLUORESCENCE AND PHOSPHORESCENCE DETECTION METHOD, AND PAPER-SHEET PROCESSING DEVICE

BACKGROUND OF THE INVENTION

1. Field of the Invention

The present invention relates to a fluorescence and phosphorescence detection device, a fluorescence and phosphorescence detection method, and a paper-sheet processing device equipped with a fluorescence and phosphorescence detection device capable of detecting fluorescence emission and phosphorescence emission that are excited on a paper sheet in order to recognize the paper sheet.

2. Description of the Related Art

Conventionally, a security mark having a certain optical property is used for authenticating a paper sheet. For example, such a security mark is prepared with a special material that does not emit light when irradiated with a visible light but emits light only when irradiated with an excitation light of a predetermined wavelength. By arranging such a security mark on a paper sheet, it is possible to authenticate the paper sheet based on an emission state of the security mark when the security mark is irradiated with the excitation light. Moreover, a plurality of such security marks having different emission properties can be provided on a single paper sheet. For example, one security mark may show fluorescence emission in which the security mark performs emission only while it is being irradiated with the excitation light, and another security mark may show phosphorescence emission. In the phosphorescence emission, the security mark continues emitting even after the irradiation of the excitation light thereon has been stopped, but the emission intensity gradually attenuates as time passes.

Japanese Patent No. JP4048121 discloses a method of detecting the phosphorescence emission from a security mark. This method involves to determine the presence/absence of the phosphorescence emission based on one emission intensity measured while the security mark is being irradiated with an excitation light and the other emission intensity measured after the irradiation of the excitation light is stopped. Japanese Patent No. JP5172066 discloses a method of signal processing that allows to determine the presence/absence of the phosphorescence emission with high precision. This method involves detection of the phosphorescence emission using previously prepared reference emission function corresponding to the phosphorescence emission, that is, normalizing the reference emission function and a measurement emission function obtained by measuring the actual phosphorescence emission, and comparing the normalized functions.

Even for the same fluorescence emission, depending on the composition of the ink that performs the emission, the wavelength band or the emission intensity of the excited fluorescence can be different. International Patent Publication No. WO2011/114455 discloses a method of detecting a plurality of emissions by using a single sensor having four photodetection elements. In this method, a visible light of a first wavelength band is detected in a first photodetection element among the four photodetection elements, and a visible light of a second wavelength band, which is different from the first wavelength band, is detected in a second photodetection element. Accordingly, two inks that excite different emissions can be distinguished based on the measurement results obtained for different wavelength bands in the first photodetection element and the second photodetection element. In this structure, the remaining third photodetection element and the fourth photodetection element detect a visible light of the entire visible wavelength band, including the first wavelength band and the second wavelength band. The measurement results obtained from the first photodetection element and the second photodetection element are corrected by using the measurement results obtained from the third photodetection element and the fourth photodetection element. This structure allows detection of each of the two inks with high precision.

However, in the above-mentioned conventional technology, it is difficult to measure with high precision both the fluorescence emission and the phosphorescence emission by one sensor. Specifically, even if the same excitation light is used, the emission quantities of the excited fluorescence emission differs from the excited phosphorescence emission greatly. Accordingly, if the conventional method that takes into account either the fluorescence emission or the phosphorescence emission is applied as it is, it is difficult to detect each emission with high precision. Therefore, there was a need for an inexpensive and small fluorescence and phosphorescence detection device capable of detecting the fluorescence emission and the phosphorescence emission with high precision.

SUMMARY OF THE INVENTION

The present invention has been made to solve the problems in the above-mentioned conventional technology. It is an object of the present invention to provide a fluorescence and phosphorescence detection device, a fluorescence and phosphorescence detection method, and a paper-sheet processing device equipped with a fluorescence and phosphorescence detection device capable of detecting fluorescence emission and phosphorescence emission from a partial region, such as a security mark, on a paper sheet, with high precision.

To solve the above problems and to achieve the object, a fluorescence and phosphorescence detection device according to an aspect of the present invention includes a fluorescence and phosphorescence sensor including a light source that emits an excitation light of a predetermined wavelength on a paper sheet, and a photodetection unit that detects fluorescence emission and phosphorescence emission excited from the paper sheet by the emission of the excitation light; a data acquiring unit that acquires a time-series waveform of a signal outputted from the fluorescence and phosphorescence sensor in response to detection of the emission in the photodetection unit; and an emission detecting unit that detects the fluorescence emission from the time-series waveform corresponding to a period in which the excitation light is emitted from the light source and detects the phosphorescence emission from an attenuation curve appearing on the time-series waveform corresponding to a period in which emission of the excitation light from the light source is stopped.

In the above fluorescence and phosphorescence detection device, the fluorescence and phosphorescence sensor includes a plurality of the photodetection units, the data acquiring unit acquires the time-series waveform for each photodetection unit, and the emission detecting unit detects for each photodetection unit the fluorescence emission and the phosphorescence emission from the time-series waveform corresponding to each photodetection unit.

In the above fluorescence and phosphorescence detection device, the fluorescence and phosphorescence sensor includes a plurality of photodetection filters, each photodetection filter arranged corresponding to each photodetection unit and allows an emission of only a predetermined wavelength band corresponding to each phot detecting filter to pass therethrough.

In the above fluorescence and phosphorescence detection device, the data acquiring unit changes an amplification factor of a signal outputted from the fluorescence and phosphorescence sensor depending on whether a measurement object of the signal is the fluorescence emission or the phosphorescence emission.

In the above fluorescence and phosphorescence detection device, the data acquiring unit includes two separate amplifier circuits of an amplifier circuit for the fluorescence emission and an amplifier circuit for the phosphorescence emission.

In the above fluorescence and phosphorescence detection device, the data acquiring unit includes one amplifier circuit, and the data acquiring unit changes an amplification factor of the amplifier circuit depending on whether the measurement object of the signal is the fluorescence emission or the phosphorescence emission.

The above fluorescence and phosphorescence detection device further includes a light-source control unit that controls a light quantity of the excitation light emitted from the light source depending on whether the measurement object on the paper sheet is the fluorescence emission or the phosphorescence emission.

In the above fluorescence and phosphorescence detection device, the light-source control unit controls the light source such that, while performing one measurement in a region on the paper sheet, the light source first emits the excitation light at a light quantity required to excite the fluorescence emission and then emits the excitation light at a light quantity required to excite the phosphorescence emission.

In the above fluorescence and phosphorescence detection device, an inclination of the attenuation curve is used as a feature amount of the attenuation curve.

In the above fluorescence and phosphorescence detection device, a time constant obtained by approximating the attenuation curve with an exponential function is used as a feature amount of the attenuation curve.

In the above fluorescence and phosphorescence detection device, the light-source control unit controls a light quantity of the excitation light for exciting the phosphorescence emission based on a signal outputted from the fluorescence and phosphorescence sensor upon measuring the fluorescence emission excited by the excitation light and a signal outputted from the fluorescence and phosphorescence sensor upon measuring the phosphorescence emission in a region in which the fluorescence emission was excited.

A paper-sheet processing device according to another aspect of the present invention includes the above fluorescence and phosphorescence detection device.

A fluorescence and phosphorescence detection method according to still another aspect of the present invention includes acquiring a time-series waveform of a signal outputted from a fluorescence and phosphorescence sensor measuring emission excited on a paper sheet, the fluorescence and phosphorescence sensor including a light source that emits an excitation light of a predetermined wavelength on the paper sheet, and a photodetection unit that detects fluorescence emission and phosphorescence emission excited from the paper sheet by the emission of the excitation light; detecting by using an emission detecting unit the fluorescence emission from the time-series waveform corresponding to a period in which the excitation light is emitted from the light source; and detecting by using the emission detecting unit the phosphorescence emission from an attenuation curve appearing on the time-series waveform corresponding to a period in which emission of the excitation light from the light source is stopped.

According to one aspect of the present invention, not only it can be determined whether the excited emission is the fluorescence emission or the phosphorescence emission based on the timing of emission of the excitation light and the timing of detection of the excited emission as in the conventional technology, but also the phosphorescence emission can be detected based on a feature of the attenuation curve appearing on the time-series waveform obtained by detecting the phosphorescence emission. Therefore, it is possible to distinguish among a plurality of types of phosphorescence emissions. For example, an inclination of an attenuation curve or a time constant obtained by approximating the attenuation curve with an exponential function can be obtained as the feature amount, and the authenticity of the banknote can be determined based on a comparison of this feature amount with that of an genuine banknote. Accordingly, the fluorescence and phosphorescence detection device can be used as a simple type banknote authentication device.

According to another aspect of the present invention, the fluorescence and phosphorescence sensor includes a plurality of the photodetection elements and, for example, each photodetection element detects a different wavelength band. Accordingly, the emission excited at different wavelength bands can be detected simultaneously. Because bandpass filters are used as the photodetection filters at the position corresponding to the photodetection elements, the emission excited at different wavelength bands can be detected separately.

Moreover, according to still another aspect of the present invention, a signal outputted from the fluorescence and phosphorescence sensor can be amplified at different amplification factors depending on whether the measurement object is the fluorescence emission or the phosphorescence emission. Accordingly, a situation, in which measurement of fluorescence emission cannot be correctly performed because the light quantity of the excitation light was adjusted for obtaining an appropriate magnitude signal for measuring the phosphorescence emission and therefore the output signal of the photodetection element of the sensor or the amplifier for the photodetection element became saturated when measuring the fluorescence emission, can be avoided. Also, a situation, in which a sufficient magnitude of phosphorescence signal cannot be obtained from the sensor because the light quantity of the excitation light was adjusted for obtaining an appropriate magnitude signal for measuring the fluorescence emission, can be avoided from occurring.

Moreover, according to still another aspect of the present invention, the amplification factor of the input signal can be changed, depending on the type of the emission to be detected, by using one amplifier circuit. Therefore, undesirable situations such as occurrence of variations from circuit to circuit, or an increase in the scale of a device or the cost of the device when a plurality of the amplifier circuits is used can be prevented.

Moreover, according to still another aspect of the present invention, by controlling the light source, the light quantity of the excitation light for obtaining the fluorescence emission and the light quantity of the excitation light for obtaining the phosphorescence emission can be set to different values. Accordingly, the light quantity of the excitation light can be adjusted such that both output signals of the fluorescence and phosphorescence sensor can be obtained in sufficient magnitude respectively. For example, while performing one measurement to detect the emission in the same light emitting region, by controlling the light source such that an integral value of the signal waveform of the fluorescence emission and an integral value of the signal waveform of the phosphorescence emission become substantially equal, both the fluorescence emission and the phosphorescence emission can be measured with high precision.

BRIEF DESCRIPTION OF DRAWINGS

FIG. 1 is a schematic structural diagram of a banknote processing device that uses a fluorescence and phosphorescence detection device according to an embodiment of the present invention.

FIG. 2 is a schematic functional block diagram of the fluorescence and phosphorescence detection device.

FIGS. 3A and 3B are schematic structural diagrams of a fluorescence and phosphorescence sensor.

FIGS. 5A and 5B show examples of a signal amplifier circuit that amplifies a signal outputted from the fluorescence and phosphorescence sensor.

FIGS. 7A to 7E are timing charts for explaining a method to measure both fluorescence emission and phosphorescence emission while controlling a light quantity of an excitation light emitted from the light source.

EMBODIMENTS

Figure 4A:
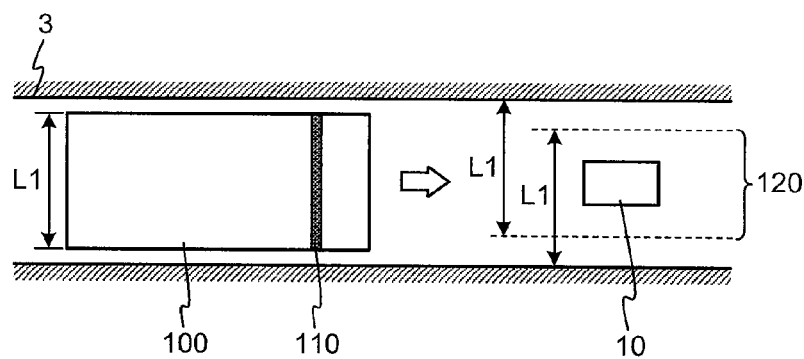
FIGS. 4A to 4D are schematic diagrams for explaining examples of arrangement of the fluorescence and phosphorescence sensor on a transport path.

Exemplary embodiments of a fluorescence and phosphorescence detection device, a fluorescence and phosphorescence detection method, and a paper-sheet processing device according to the present invention are explained below while referring to the accompanying drawings. The fluorescence and phosphorescence detection device according to the present invention has a function to detect fluorescence emission and phosphorescence emission excited on a paper sheet. The detection result obtained by the fluorescence and phosphorescence detection device is used to determine the genuiness and the like of the paper sheet. Fluorescence is a real-time emission that begins to emit as soon as the excitation is started and disappears as soon as the excitation is stopped. In contrast, phosphorescence is an emission having a time lag. An intensity of the phosphorescence emission gradually increases after the excitation is started, and the emission can be observed even after the excitation is stopped. Therefore, the phosphorescence is also called "afterglow".

First, an outline of the fluorescence and phosphorescence detection device will be given. The fluorescence and phosphorescence detection device includes a fluorescence and phosphorescence sensor to detect the fluorescence emission and the phosphorescence emission. The fluorescence and phosphorescence sensor includes a light source that emits a predetermined excitation light toward a paper sheet, four photodetection elements that respectively outputs a signal corresponding to the light emission excited on the paper sheet, and four photodetection filters, each corresponding to one of the photodetection elements, that respectively selects the emission to be received by the corresponding one of the photodetection elements. In the fluorescence and phosphorescence detection device, the fluorescence emission and the phosphorescence emission are detected by performing control of an emission timing and a light quantity, control of an amplification factor of a signal outputted from each of the photodetection elements upon detecting the emission from the paper sheet, and the like. Accordingly, it is possible to distinguish each type among a plurality of types of emissions based on a wavelength band, an emission quantity, a time-series waveform indicating a change in an emission intensity, and the like, of the emission excited on the paper sheet.

The fluorescence and phosphorescence detection device can handle various types of paper sheets such as banknotes, checks, other valuable securities, and the like, as a processing object. Moreover, the processing object is not limited to a paper sheet as long as the fluorescence emission and the phosphorescence emission can be excited. For example, the processing object can be coins and the like. The processing object of the paper-sheet processing device that uses the fluorescence and phosphorescence detection device is also not limited to a certain type of paper sheets; however, in the present embodiment, the fluorescence and phosphorescence detection device is used in a banknote processing device (paper-sheet processing device), which processes banknotes, to determine the authenticity of the banknotes.

FIG. 1 is a schematic structural diagram of the banknote processing device that uses a fluorescence and phosphorescence detection device 1 according to an embodiment of the present invention. The banknote processing device includes a money inlet 2 in which a plurality of banknotes can be stacked, a transport path 3 to transport the banknotes one by one from the money inlet 2 to the inside of the device, the fluorescence and phosphorescence detection device 1 that excites the fluorescence emission and the phosphorescence emission on the banknote that is transported over the transport path 3 and detects the fluorescence emission and the phosphorescence emission, a storage unit 4 for storing therein banknotes that can be stored inside the device, and a reject unit 5 for discharging reject banknotes such as counterfeit banknotes and banknotes that cannot be recognized.

Additionally, the banknote processing device includes a recognition unit. The recognition unit has a function to recognize a kind (denomination, old/new version, etc.), genuiness, fitness, orientation, and the like of a banknote. The recognition unit performs a recognition process by using a recognition sensor such as a line sensor, a magnetic sensor, and a thickness sensor. For example, the fluorescence and phosphorescence detection device 1 is used to add a function to the recognition unit to enhance the recognition precision of the banknotes. The recognition unit and the fluorescence and phosphorescence detection device 1 can be arranged separately, or the fluorescence and phosphorescence detection device 1 can be arranged inside the recognition unit. For example, the below-explained structure for detecting the fluorescence emission and the phosphorescence emission is added to a conventional recognition unit to realize an improved recognition unit that can function also as the fluorescence and phosphorescence detecting device 1. In the following explanation, the details of the conventional technology including the structure of the recognition unit will be omitted, and detailed explanation of the fluorescence and phosphorescence detection device 1 will be given.

FIG. 2 is a schematic functional block diagram of the fluorescence and phosphorescence detection device 1. The fluorescence and phosphorescence detection device 1 includes a fluorescence and phosphorescence sensor 10, a control unit 30, and a memory unit 40. A CPU is used in the control unit 30, for example. The control unit 30 includes a transport information acquiring unit 31, a light-source control unit 32, a data acquiring unit 33, and a recognition processing unit 34. The fluorescence and phosphorescence sensor 10 includes four detecting elements that are a first photodetection element 11, a second photodetection element 12, a third photodetection element 13, a fourth photodetection element 14, and one light source 15; however, the details will be given later. Although a structure that includes four photodetection elements and four photodetection filters is explained below, the number of the photodetection elements and the photodetection filters is not limited. That is, the structure may include a plurality of the photodetection elements and the photodetection filters. Also, the structure may include one photodetection element and one photodetection filter. When the fluorescence and phosphorescence detection device 1 is arranged inside the recognition unit, the control unit 30 and the memory unit 40 may be integrated within the recognition unit.

The transport information acquiring unit 31, same as in the conventional technology, has a function to obtain information about a denomination, an orientation, and the like of a banknote from the recognition unit, which identify the denomination, the genuiness and the like. Moreover, the transport information acquiring unit 31 has a function to identify a position of the banknote on the transport path 3.

The light-source control unit 32 has a function to control the operation of the light source 15 based on the position of the banknote on the transport path 3 identified by the transport information acquiring unit 31. Moreover, the light-source control unit 32 has a function to control a light quantity, that is, a light intensity and a light emission time, of an excitation light that is emitted from the light source 15 towards the banknote.

The data acquiring unit 33 has a function to control the first to fourth photodetection elements 11 to 14 based on the position of the banknote on the transport path 3 identified by the transport information acquiring section 31 and acquire data relating to the optical properties of the banknote. The data acquiring unit 33 includes an amplifier circuit and an A/D converter, and has a function to adjust a gain for a signal outputted from the respective first to fourth photodetection elements 11 to 14. The fluorescence and phosphorescence detection device 1 previously acquires information on an emission quantity of the emission excited on the banknote and, by adjusting based on the acquired information on at least one of a light quantity of the excitation light emitted from the light source 15 and the gain of a signal outputted from the sensor, a strength of the signal acquired from the banknote can be adjusted.

The recognition processing unit 34 has a function to recognize the kind and the orientation of the banknote before the banknote being transported reaches a measurement position on the transport path 3 at which the fluorescence and phosphorescence sensor 10 performs the measurement. Based on the recognition result, measurement using the fluorescence and phosphorescence sensor 10 is carried out by the light-source control unit 32 and the data acquiring unit 33. Moreover, the recognition processing unit 34 has a function to detect the fluorescence emission and the phosphorescence emission based on the data acquired by using the fluorescence and phosphorescence sensor 10, and determine the genuiness of the banknote and the like. In other words, the recognition processing unit 34 has functions of an emission detecting unit, which detects the fluorescence emission and the phosphorescence emission, and a banknote recognition unit.

The method of recognizing the kind and the orientation of the banknote is not particularly limited. For example, the recognition unit arranged upstream of the fluorescence and phosphorescence sensor 10 in the transport direction can recognize the kind of banknotes, such as the denomination and the old/new version, and also recognize a transportation state of the banknote. The recognition of the transportation state includes recognizing whether the banknote is being transported with the face side up or the back side up, and recognizing whether the banknote is being transported with the portrait upright or the portrait inverted when viewed from above. The recognition processing unit 34 may recognizes the kind and the orientation of the banknote based on the recognition result obtained in the recognition unit. Alternatively, for example, the recognition processing unit 34 may use recognition sensors such as a line sensor, a magnetic sensor, and a thickness sensor, arranged upstream of the fluorescence and phosphorescence sensor 10 in the transport direction to recognize the kind and the orientation of the banknote. In this case, the recognition unit, which includes the recognition sensors, and the fluorescence and phosphorescence sensor 10 may be arranged as separate components, or the recognition unit may include both the recognition sensors and the fluorescence and phosphorescence sensor 10. By recognizing the kind and the orientation of the banknote being transported on the transport path 3, the recognition processing unit 34 can identify the type of emission, such as the fluorescence emission or the phosphorescence emission, excited on the banknote and a partial region on the banknote from where the light emission is excited, and determine the method of measurement of the emission. Thereafter, the light-source control unit 32 controls the light source 15 to emit the excitation light at a timing at which the predetermined partial region on the banknote passes. The data acquiring unit 33 acquires data to determine whether the predetermined emission is excited in the predetermined partial region on the banknote.

The memory unit 40 is a nonvolatile storage device, such as a semiconductor memory, capable of storing therein a data on an emission measurement condition 41 and a recognition data 42. The light-source control unit 32 and the data acquiring unit 33 operate based on the emission measurement condition 41.

The emission measurement condition 41 is information that information necessary to acquire data relating to the emission from the partial region on the banknote and information for identifying a timing of turning on the light source 15, a timing of turning off the light source 15 that has been turned on, and the like are correlated. The emission measurement condition 41 also includes information about a light quantity of the excitation light to be emitted from the light source 15, a timing when the data acquiring unit 33 is to acquire an output signal from the respective first to fourth photodetection elements 11 to 14, an amount of the gain adjustment of the output signal, and the like. In other words, at least one of the light quantity of the excitation light emitted from the light source 15 and the strength of a signal acquired from the sensor can be adjusted based on the emission measurement condition 41. This adjustment is performed based on the type, light quantity and the like of the emission observed on the banknote.

The recognition data 42 is data used to determine the genuineness and the like of the banknote based on the data obtained by the fluorescence and phosphorescence sensor 10. For example, for each kind of banknote, information relating to the data obtained from the banknote by the fluorescence and phosphorescence sensor 10 is previously stored as the recognition data 42. The genuiness and the like of the banknote transported on the transport path 3 can be determined by comparing the data obtained by the fluorescence and phosphorescence sensor 10 from the banknote being transported on the transport path 3 with the data previously prepared as the recognition data 42.

FIGS. 3A and 3B are schematic structural diagrams of the fluorescence and phosphorescence sensor 10. FIG. 3A is a schematic cross-sectional diagram viewed from a side of the fluorescence and phosphorescence sensor 10. FIG. 3B shows a positional relation among the photodetection elements 11 to 14 and photodetection filters 51 to 54 when the fluorescence and phosphorescence sensor 10 is viewed from below (from the lower side of the fluorescence and phosphorescence sensor 10 shown in FIG. 3A).

As shown in FIG. 3A, the fluorescence and phosphorescence sensor 10 includes a sensor case 61, a photodiode substrate 62 on which the first to fourth photodetection elements 11 to 14 are formed, a filter frame 50 that supports the first to fourth photodetection filters 51 to 54, an ultraviolet-light reflection mirror 72, an ultraviolet-light transmission filter 71, the light source 15, and a transparent cover glass 63. As shown in FIG. 3B, the first to fourth photodetection filters 51 to 54 are arranged corresponding to the first to fourth photodetection elements 11 to 14.

The sensor case 61 is made of black resin and the like through which a light cannot pass. The light source 15, the ultraviolet-light transmission filter 71, and the ultraviolet-light reflection mirror 72 are fixed inside the sensor case 61. The photodiode substrate 62 is arranged on the top side of the sensor case 61 and the cover glass 63 is arranged on the bottom side of the sensor case 61.

The light source 15 consists of an LED that emits an ultraviolet light. The ultraviolet light emitted from the light source 15, after having passed through the ultraviolet-light transmission filter 71, is reflected by the ultraviolet-light reflection mirror 72. The reflected ultraviolet light passes through the cover glass 63 and illuminates the banknote on the transport path 3 that is present below the fluorescence and phosphorescence sensor 10. When the emission of light is excited on the banknote by illuminating with the ultraviolet light, excited light enters the sensor case 61 via the cover glass 63. The ultraviolet-light reflection mirror 72 removes an ultraviolet-light component from the entered light. Only the light that passes through the ultraviolet-light reflection mirror 72 reaches the first to fourth photodetection filters 51 to 54. Moreover, only the light that passes through the first to fourth photodetection filters 51 to 54 is detected by the first to fourth photodetection elements 11 to 14 arranged corresponding to each of the filters.

The first photodetection filter 51 is a bandpass filter through which only a light having a wavelength between 450 nanometer (nm) and 500 nm can pass. The second photodetection filter 52 is a bandpass filter through which only a light having a wavelength between 500 nm and 550 nm can pass. The third photodetection filter 53 is a bandpass filter through which only a light having a wavelength between 550 nm and 600 nm can pass. The fourth photodetection filter 54 is a bandpass filter through which only a light having a wavelength above 600 nm can pass.

As shown in FIG. 3A, the filter frame 50 supports the first to fourth photodetection filters 51 to 54 in between the ultraviolet-light reflection mirror 72 and the first to fourth photodetection elements 11 to 14. The first to fourth photodetection filters 51 to 54 are supported in such a manner that the top surfaces of these filters form one plane and the bottom surfaces of these filters form another one plane. As shown in FIG. 3B, the first to fourth photodetection elements 11 to 14 formed on the photodiode substrate 62 and the first to fourth photodetection filters 51 to 54 supported by the filter frame 50 are all arranged in a matrix of two rows and two columns. The emitted light that passes through the first photodetection filter 51 is detected by the first photodetection element 11. The emitted light that passes through the second photodetection filter 52 is detected by the second photodetection element 12. The emitted light that passes through the third photodetection filter 53 is detected by the third photodetection element 13. The emitted light that passes through the fourth photodetection filter 54 is detected by the fourth photodetection element 14. A signal representing the detected light is outputted from the respective first to fourth photodetection elements 11 to 14, and those signals are inputted into the data acquiring unit 33 shown in FIG. 2.

Each of the first to fourth photodetection elements 11 to 14 shown by a dotted line in FIG. 3B has a square shape with one side thereof having a length of approximately 3.5 millimeters (mm). Each of the first to fourth photodetection filters 51 to 54 has a square shape with one side thereof having a length of approximately 4 mm. Each of the first to fourth photodetection elements 11 to 14 and each of the first to fourth photodetection filters 51 to 54 are arranged in such a manner that a center of a light receiving surface of each photodetection element and a center of a filter surface of the corresponding photodetection filter coincide with each other. The first to fourth photodetection elements 11 to 14 arranged in the matrix of two rows and two columns are arranged within a region of a width 8 mm and a depth 8 mm.

The fluorescence and phosphorescence sensor 10 is a small-sized sensor having a width (a left-right direction in FIGS. 3A and 3B) of approximately 20 mm, a depth (an up-down direction in FIG. 3B) of approximately 12 mm, and a height (an up-down direction in FIG. 3A) of approximately 13.5 mm. By using the fluorescence and phosphorescence sensor 10 installed above the transport path 3, the light excited from the banknote being transported on the transport path 3 can be measured from a rectangular measurement region having dimensions of 8 mm×8 mm. In the fluorescence and phosphorescence detection device 1, the measurement of the fluorescence emission and the phosphorescence emission can be performed within a time period of 500 microseconds (μs). Accordingly, even if the banknote is transported at a fast speed of 2000 mm/s on the transport path 3, it is prevented that the light emitting region passes over the measurement region of the fluorescence and phosphorescence sensor 10 without the measurement being successfully performed. This allows accurate measurement of the light emission excited from the partial region on the banknote.

Specifically, by using the fluorescence and phosphorescence sensor 10, the light is excited from the measurement region on the banknote, and the light emitted from the same region passes through the first to fourth photodetection filters 51 to 54 and is detected by the first to fourth photodetection elements 11 to 14. Specifically, among the emitted lights from the same light emitting region on the banknote, the light having the wavelength between 450 nm and 500 nm is measured by the first photodetection element 11, the light having the wavelength between 500 nm and 550 nm is measured by the second photodetection element 12, the light having the wavelength between 550 nm and 600 nm is measured by the third photodetection element 13, and the light having the wavelength above 600 nm is measured by the fourth photodetection element 14.

FIGS. 4A to 4D are schematic diagrams explaining an example of arrangement of the fluorescence and phosphorescence sensor 10 on the transport path 3. For example, as shown in FIG. 4A, when a band-shaped light emitting region 110 is provided over the entire region of a banknote 100 parallel to the short edge side thereof, the fluorescence and phosphorescence sensor 10 is arranged within a region 120 orthogonal to the transport direction (hollow arrow).

If the light emitting region is not formed over the entire region of the banknote 100 in the orthogonal direction of the transport direction, the number of the fluorescence and phosphorescence sensor 10 to be arranged in the transport path 3 and the arrangement positions thereof are decided taking into consideration the positions of light emitting regions 111a to 111d passing on the transport path 3.

Figure 4B:
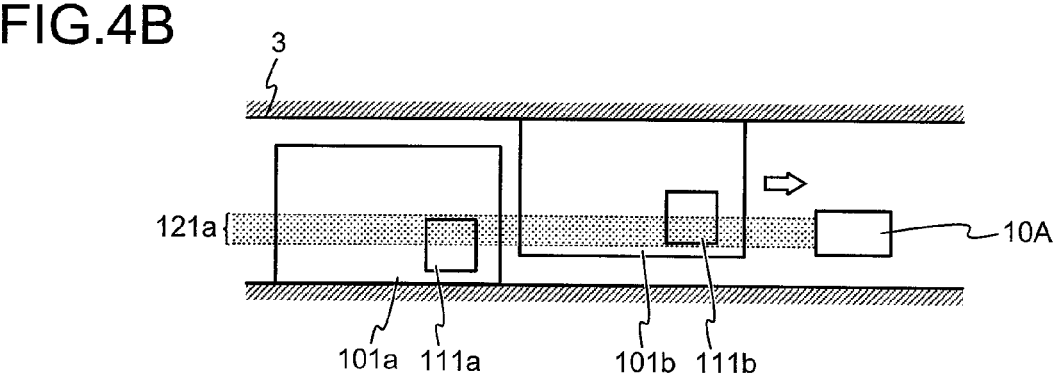
Figure 4C:
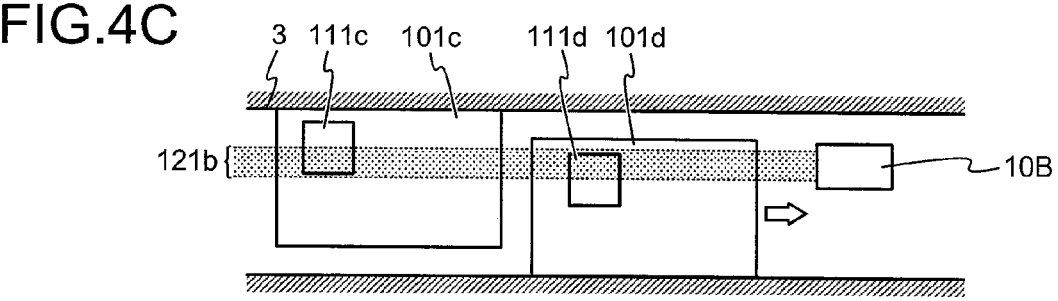
Figure 4D:
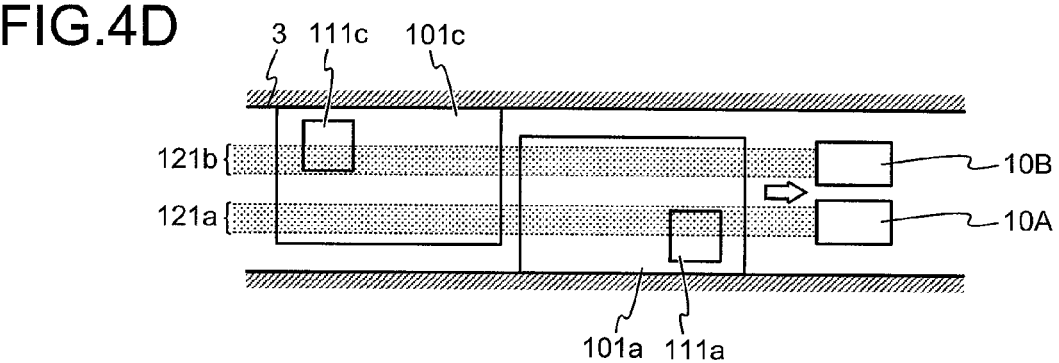

FIGS. 4B to 4D show examples of arrangement of the light emitting regions 111a to 111d that are partial regions on the banknote. When all the banknotes are transported such that the light emitting regions 111a and 111b are located in a front half portion with respect to the transport direction, the position of the banknote on the transport path 3 varies between the banknotes 101a and 101b shown in FIG. 4B in the direction orthogonal to the transport direction (hollow arrow). In this case, irrespective of the position of the banknote on the transport path 3, a fluorescence and phosphorescence sensor 10A is arranged in a region 121a such that the emitted light excited from the light emitting regions 111a and 111b can be surely measured. On the other hand, when all the banknotes are transported such that the light emitting regions 111c and 111d are located at a rear half portion with respect to the transport direction, the position of the banknote on the transport path 3 varies between the banknotes 101c and 101d shown in FIG. 4C in the direction orthogonal to the transport direction (hollow arrow). In this case, irrespective of the position of the banknote on the transport path 3, a fluorescence and phosphorescence sensor 10B is arranged in a region 121b such that the emitted light excited from the light emitting regions 111c and 111d can be surely measured. When the banknotes are transported on the transport path 3 in both situations shown in FIGS. 4B and 4C, two fluorescence and phosphorescence sensors 10A and 10B are arranged as shown in FIG. 4D. In this case, based on the recognition result of the kind, the orientation, and the like of the banknote obtained by the recognition processing unit 34, after identifying the position of the light emitting region 111a to 111d that passes, the emitted light is detected by using the fluorescence and phosphorescence sensor 10A or 10B.

In the fluorescence and phosphorescence detection device 1, the excitation light is emitted on the banknote 100 from the light source 15, and the emitted lights that has passed though the respective first to fourth photodetection filters 51 to 54 are detected by the respective first to fourth photodetection elements 11 to 14, thereby the fluorescence emission and the phosphorescence emission are measured. The gain of the signal outputted from the respective first to fourth photodetection elements 11 to 14 can be controlled by the data acquiring unit 33. The data acquiring unit 33 includes a signal amplifier circuit that adjusts the gain of the signal outputted from the respective first to fourth photodetection elements 11 to 14. However, the circuit structure is not limited to the one where the gain is adjustable, but a circuit structure is allowable in which the measurement is performed at a fixed gain.

Figure 5B:
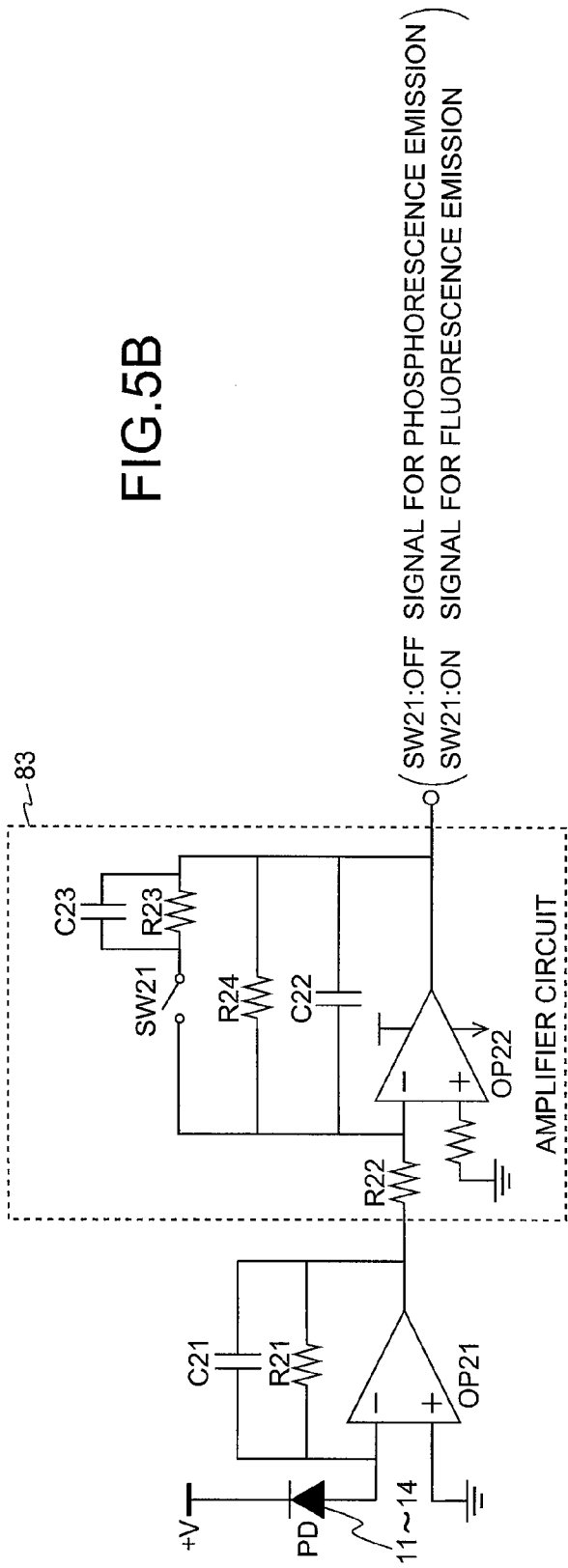

FIGS. 5A and 5B show examples of the signal amplifier circuit of the data acquiring unit 33. FIG. 5A shows an example in which a fluorescence-emission amplifier circuit 81, which is used to detect the fluorescence emission, and a phosphorescence-emission amplifier circuit 82, which is used to detect the phosphorescence emission, are provided as separate components. In contrast, FIG. 5B shows an example in which one amplifier circuit 83 can be used to detect both the fluorescence emission and the phosphorescence emission. In the circuit structure shown in FIG. 5A, the circuit to be used for the detection is changed based on the target type, the light quantity of the emission, or the like to be detected. In contrast, in the circuit structure shown in FIG. 5B, in a single circuit, the amplification factor is changed based on the target type, the light quantity of the emission, or the like to be detected. Only one circuit diagram has been shown in FIGS. 5A, 5B and 6 because the same amplifier circuit can be arranged for all of the first to fourth photodetection elements 11 to 14; however, the amplifier circuit shown here is arranged separately for each of the first to fourth photodetection elements 11 to 14.

In the example shown in FIG. 5A, upon detecting light by the first to fourth photodetection elements 11 to 14 (PD: photodiode) of the fluorescence and phosphorescence sensor 10, the signals outputted from the first to fourth photodetection elements 11 to 14 are inputted into both the fluorescence-emission amplifier circuit 81 and the phosphorescence-emission amplifier circuit 82. By appropriately selecting the capacitances of capacitors C11 to C13, resistances of resistors R11 to R15, and operational amplifiers OP11 to OP13, it is possible to set the amplification factor of the phosphorescence-emission amplifier circuit 82 several times larger than that of the fluorescence-emission amplifier circuit 81. The output value outputted from the fluorescence-emission amplifier circuit 81 is used when the emission excited on the banknote 100 is the fluorescence emission, and the output value outputted from the phosphorescence-emission amplifier circuit 82 is used when the emission excited on the banknote 100 is the phosphorescence emission. By doing so, a signal that is amplified at a higher amplification factor can be acquired for the phosphorescence emission than the one for the fluorescence emission.

In the example shown in FIG. 5B, upon detecting light by the first to fourth photodetection elements 11 to 14 (PD: photodiode) of the fluorescence and phosphorescence sensor 10, the signals outputted from the first to fourth photodetection elements 11 to 14 are inputted into the amplifier circuit 83 irrespective of whether the signal is obtained by measuring the fluorescence emission or the phosphorescence emission. By appropriately selecting the capacitances of capacitors C21 to C23, and the resistances of resistors R21 to R24, for example, an amplification factor when a switch SW21 is switched off can be set several times larger than that when the switch SW21 is switched on. Specifically, the amplification factor can be changed by controlling the switch SW21 to change a resistance decided by the resistors R23 and R24 between an inverting g input terminal and an output terminal of an operational amplifier OP22. When the light emission excited on the banknote 100 is the fluorescence emission, the switch SW21 is switched on and an output value outputted from the amplifier circuit 83 having a lower amplification factor is used. In contrast, when the light emission excited on the banknote 100 is the phosphorescence emission, the switch SW21 is switched off and an output value outputted from the amplifier circuit 83 having a higher amplification factor is used. By doing so, a signal that is amplified at the higher amplification factor can be acquired when detecting the phosphorescence emission than when detecting the fluorescence emission. In this manner, by using a common circuit for detecting both the phosphorescence emission and the fluorescence emission, the number of parts can be reduced. Moreover, the influence of the variations in parts can be suppressed in comparison to a case where separate circuits are arranged. Accordingly, even if the signal is weak, the signal can be measured with high precision.

In the fluorescence and phosphorescence detection device 1, by controlling the light quantity of the excitation light emitted from the light source 15 of the fluorescence and phosphorescence sensor 10 by the light-source control unit 32, it is possible to adjust the output values of the signals outputted from the first to fourth photodetection elements 11 to 14.

Figure 6:
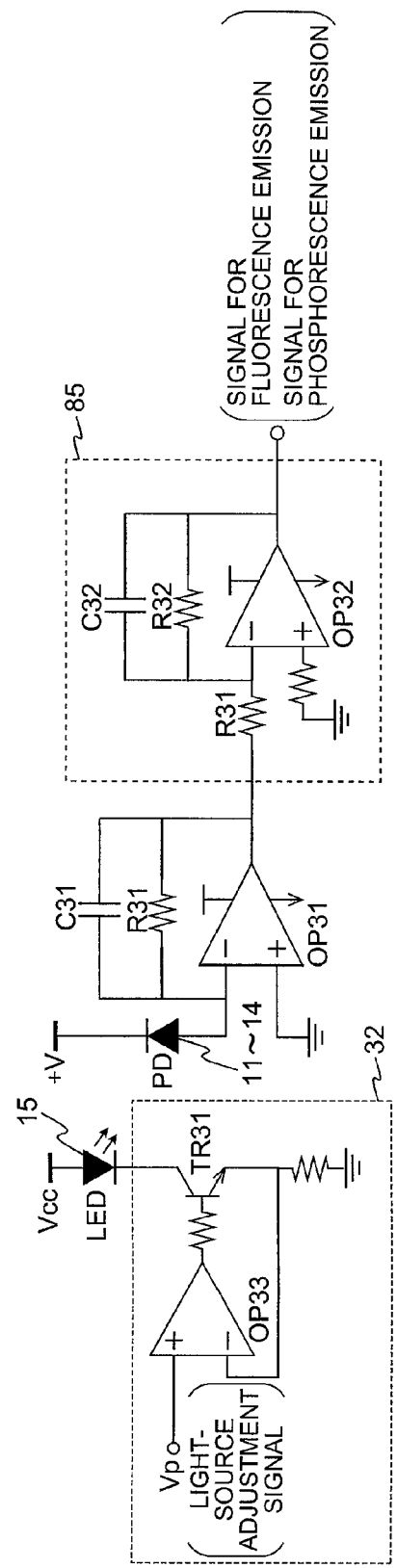
FIG. 6 shows an example of a circuit that controls a light quantity of an excitation light emitted from a light source.

FIG. 6 shows an example of a circuit that controls the light quantity of the excitation light emitted from the light source 15 thereby controlling the output values of the signals outputted from the first to fourth photodetection elements 11 to 14. The light quantity of the excitation light emitted from the LED of the light source 15 can be controlled by inputting a light-source adjustment signal Vp into a transistor TR31 of the light-source control unit 32. For example, by connecting an analog output terminal of a D/A converter to an input terminal of an operational amplifier OP33 of which output terminal is connected via a base resistor to abase terminal of the transistor TR31 in an emitter follower circuit, and by controlling the light-source adjustment signal Vp inputted to the analog output terminal, a light emission current supplied to the LED can be controlled. Based on whether the light emission excited on the banknote 100 is the fluorescence emission or the phosphorescence emission, the light quantity of the excitation light is changed by controlling the light emission current supplied to the LED. Specifically, the light quantity of the excitation light is controlled, so that both the signals outputted from the first to fourth photodetection elements 11 to 14 when measuring the fluorescence emission and when measuring the phosphorescence emission can be obtained as signals of appropriate magnitude. The same amplification factor is used in an amplifier circuit 85 to amplify the signals outputted from the first to fourth photodetection elements 11 to 14 (PD) for the fluorescence emission and for the phosphorescence emission. For example, the phosphorescence-emission amplifier circuit 82 shown in FIG. 5A can be used as the amplifier circuit 85 shown in FIG. 6.

In this manner, in the fluorescence and phosphorescence sensor 10, apart from controlling the gain of the signals outputted from the first to fourth photodetection elements 11 to 14, the light quantity of the excitation light emitted from the light source 15 is controlled to obtain sufficient signal outputs from the first to fourth photodetection elements 11 to 14. In this process, if only the light quantity of the excitation light is set to obtain the sufficient signal outputs for the phosphorescence emission, the emission quantity of the fluorescence emission also increases. Accordingly, outputs from photodetection elements that constitute the first to fourth photodetection elements 11 to 14 or amplifiers for them become saturated and there may be situations where accurate measurement cannot be performed for the fluorescence emission. In the fluorescence and phosphorescence detection device 1, the light-source control unit 32 controls the light source 15 so that such a situation does not occur.

Figures 7B, 7C, 7D, 7E:
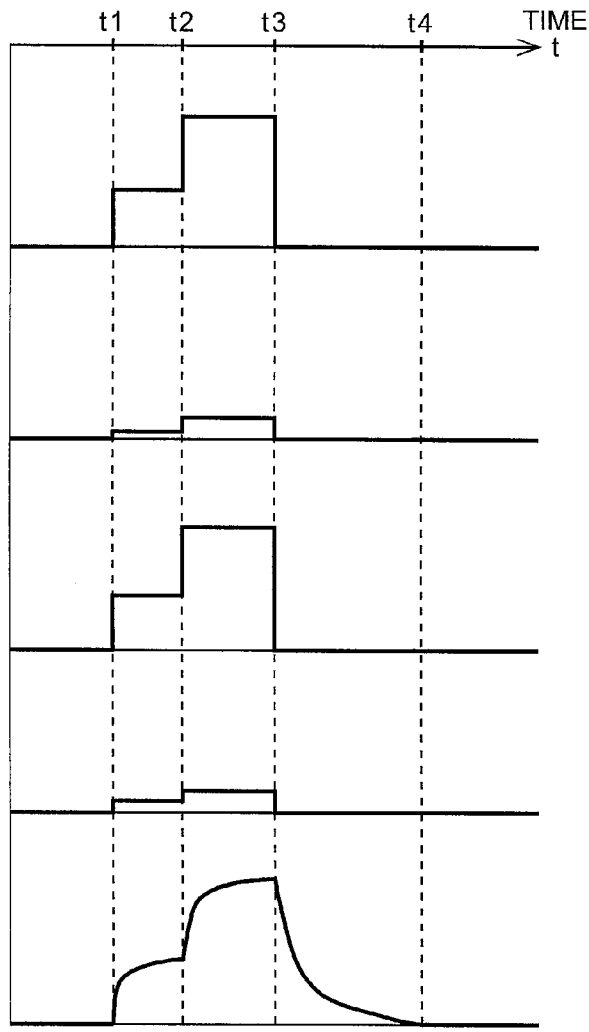

FIGS. 7A to 7E are timing charts for explaining a method to measure both the fluorescence emission and the phosphorescence emission while the light-source control unit 32 is controlling the light quantity of the excitation light emitted from the light source 15. In the examples shown in FIGS. 7A to 7E, it is assumed that, when the excited light emission region 110 on the banknote 100 is irradiated with the ultraviolet light as the excitation light, the fluorescence emission of the wavelength between 500 nm and 550 nm and the phosphorescence emission of the wavelength above 600 nm are excited. When the ultraviolet light is emitted by controlling the light source 15 as shown in FIG. 7A, the time-series waveforms of the signals outputted from the first to fourth photodetection elements 11 to 14 are shown as FIGS. 7B to 7E. In FIGS. 7A to 7E, the horizontal axis represents time, and the vertical axis in FIG. 7A represents a light emission current applied to the LED of the light source 15. FIGS. 7B to 7E show the signals outputted from the first to fourth photodetection elements 11 to 14.

As shown in FIG. 7A, the light-source control unit 32 controls the light emission current as to the light quantity of the light source 15 so that the light emission current waveform shown as time-series data is a stepped waveform having two steps. Specifically, between time points t1 and t2, the light quantity of the excitation light emission current of the light source 15 is controlled such that the fluorescence emission is excited and signals of appropriate values are outputted from the first to fourth photodetection elements 11 to 14 when a normal banknote is used as a banknote to be recognized. The data acquiring unit 33 performs the measurement of the fluorescence emission between the time points t1 and t2. After completion of the measurement of the fluorescence emission, between time points t2 and t3, the light quantity of the excitation light emitted from the light source 15 is controlled such that the phosphorescence emission is emitted with sufficient emission quantity. Specifically, to obtain the signal outputs of the appropriate values from the first to fourth photodetection elements 11 to 14 between time points t3 and t4 where the measurement of the phosphorescence emission is performed, the light-source control unit 32 controls the light quantity of the excitation light emitted from the light source 15 so that the light quantity between the time points t2 and t3 is higher than that between the time points t1 and t2. The light-source control unit 32 turns off the light source 15 at the time point t3. After the light source 15 has been turned off, the data acquiring unit 33 measures the phosphorescence emission between the time points t3 and t4. In the data acquiring unit 33, a sampling period can be set as desired between 1 µs and 100 µs, and the measurement is performed by using appropriate sampling periods set beforehand between the time points t1 and t2 and between the time points t3 and t4. As to determination of the excitation light emitting currents of the light source 15 for controlling the light quantity of the exciting light, time points to sample the signal of the waveform and circuit constants, optimal values to obtain emission light quantity of fluorescence emission and phosphorescence emission are derived and stored in the memory 40 beforehand. Such optimal values are derived from learning by collecting sampling data from normal banknotes to be recognized for respective types and respective transporting directions while changing the emission current for each set among several possible sets of circuit constants. When banknote recognition is performed, the values of the emission current and the time points and the like are obtained and used from the memory 40 based on the recognition result relating to a denomination and a transporting direction of the banknote. Furthermore, for an example, the time point t1 may be determined after the banknote has been transported for a predetermined distance from a presence detection sensor which is disposed upstream of the fluorescence and phosphorescence sensor 10 in the transport path and detects the arrival of the banknote.

In the examples shown in FIGS. 7A to 7E, as shown in FIGS. 7B and 7D, the signal outputted from the first photodetection element 11 for measuring the emission of the wavelength band 450 nm to 500 nm that has passed through the first photodetection filter 51 is almost zero, and the signal outputted from the third photodetection element 13 for measuring the emission of the wavelength band 550 nm to 600 nm that has passed through the third photodetection filter 53 is also almost zero. Those indicate that no emission is detected by the elements.

In contrast, as shown in FIG. 7C, the measurement result of the second photodetection element 12 for measuring the emission of the wavelength band 500 nm to 550 nm that has passed through the second photodetection filter 52 is obtained that the fluorescence emission is detected. When the measurement result of the second photodetection element 12 is obtained as shown FIG. 7C, the data acquiring unit 33 uses only the signal output between the time points t1 and t2, and does not use the signal output between the time points t2 and t3. The reason is that, the light quantity of the excitation light emitted from the light source 15 between the time points t2 and t3 is too large, whereby the output of the photodetection element constituting the second photodetection element 12 or the amplifier for the second detection unit element 12 becomes saturated and accurate measurement cannot be performed.

As shown in FIG. 7E, the measurement result of the fourth photodetection element 14 for measuring the emission of the wavelength band above 600 nm that has passed through the fourth photodetection filter 54 is obtained that the phosphorescence emission is detected. When the measurement result of the fourth photodetection element 12 is obtained as shown FIG. 7E, the data acquiring unit 33 uses only the signal output between the time points t1 and t2 and the signal output between the time points t3 and t4, and does not use the signal output between the time points t2 and t3. A signal is outputted from the fourth photodetection element 14 even between the time points t1 and t2; however, the data acquiring unit 33 uses the measurement result between the time points t3 and t4, which is obtained after the light source 15 is turned off, for detecting the phosphorescence emission.

The recognition processing unit 34 (a light emission detection unit) detects the fluorescence emission and the phosphorescence emission based on the signal between the time points t1 and t2, and the signal between the time points t3 and t4, which are acquired by the data acquiring unit 33 by using the first to fourth photodetection elements 11 to 14. Specifically, because a signal indicating the emission is outputted from the second photodetection element 12 between the time points t1 and t2 but a signal indicating no emission is outputted between the time points t3 and t4, it is determined that the fluorescence emission having the wavelength between 500 nm and 550 nm is excited. Moreover, because a signal indicating the emission is outputted from the fourth photodetection element 14 between the time points t1 and t2, and in addition, a signal indicating the emission is also outputted between the time points t3 and t4, it is determined that the phosphorescence emission having the wavelength above 600 nm is excited. Moreover, the recognition processing unit 34 determines that in the wavelength between 450 nm and 500 nm, and in the wavelength between 550 nm and 600 nm, no emission is detected.

The light quantity of the excitation light emitted from the light source 15 between the time points t1 and t2 shown in FIG. 7A is adjusted and determined previously, based on the fluorescence emission measured between the time points t1 and t2 shown in FIG. 7C so that an output signal of a sufficient magnitude is obtained from the second photodetection element 12 without the output of the second photodetection element 12 or the amplifier for the second photodetection element 12 becoming saturated. Similarly, the light quantity of the excitation light emitted from the light source 15 between the time points t2 and t3 shown in FIG. 7A is adjusted and determined previously, based on the afterglow measured between the time points t3 and t4 shown in FIG. 7E so that an output signal of a sufficient magnitude is obtained from the fourth photodetection element 14.

Specifically, as the light emission measurement condition 41, information on the integrated value of the light emission measured between the time points t1 and t2 and the integrated value of the light emission measured between the time points t3 and t4, which are shown in FIGS. 7C and 7D, are previously stored in the memory unit 40 in a correlated manner with the kind, the orientation, and the like of the banknotes. After recognizing the kind, the orientation, and the like of the banknote being transported on the transport path 3, the stored data on the integrated value of light emission that corresponds to the recognition result is retrieved, and the light quantity of the excitation light is adjusted based on the retrieved data. If a plurality of the fluorescence and phosphorescence sensors 10 is used, such as the sensors 10A and 10B shown in FIG. 4D, information required to perform the adjustment of the light quantity can be stored in the memory unit 40 in a correlated manner with the sensor number. By doing so, based on the data prepared for each sensor number, the light quantity of the excitation light can even be adjusted separately in each of the sensors 10A and 10B.

When performing the measurement in the fluorescence and phosphorescence detection device 1, for example, the kind, the transport direction, and the like of the banknote 100 are identified based on a recognition result of the banknote 100 obtained earlier by using the conventional recognition sensor. The light-source control unit 32 and the data acquiring unit 33 retrieve from the memory unit 40 the emission measurement condition 41 corresponding to the identified information of the banknote 100. And, based on the retrieved emission measurement condition 41, the control of the light source 15 by the light-source control unit 32 and the measurement by the data acquiring unit 33 by using the first to fourth photodetection elements 11 to 14 are performed.

When the measurement result of the emission is obtained by the data acquiring unit 33, based on this measurement result, the recognition processing unit 34 determines whether the emission is detected by the first to fourth photodetection elements 11 to 14, and performs the recognition process of the authenticity and the like of the banknote 100 based on the type of the detected emission. The recognition process is performed by comparison with the data previously stored in the memory unit 40 as the recognition data 42. For example, the fluorescence emission can be detected from the predetermined excited light emission region on the banknote 100 based on the recognition result of the banknote 100, the recognition process of the authenticity of the banknote 100 is performed based on the wavelength band of the detected fluorescence emission, the emission quantity of the fluorescence emission, and the like.

Moreover, with respect to the phosphorescence emission also, the recognition process is performed based on the wavelength band and the emission quantity of the detected phosphorescence emission. In the fluorescence and phosphorescence detection device 1, in addition to the above, the recognition process can be performed based on a signal waveform obtained by measuring the afterglow.

Figure 8:
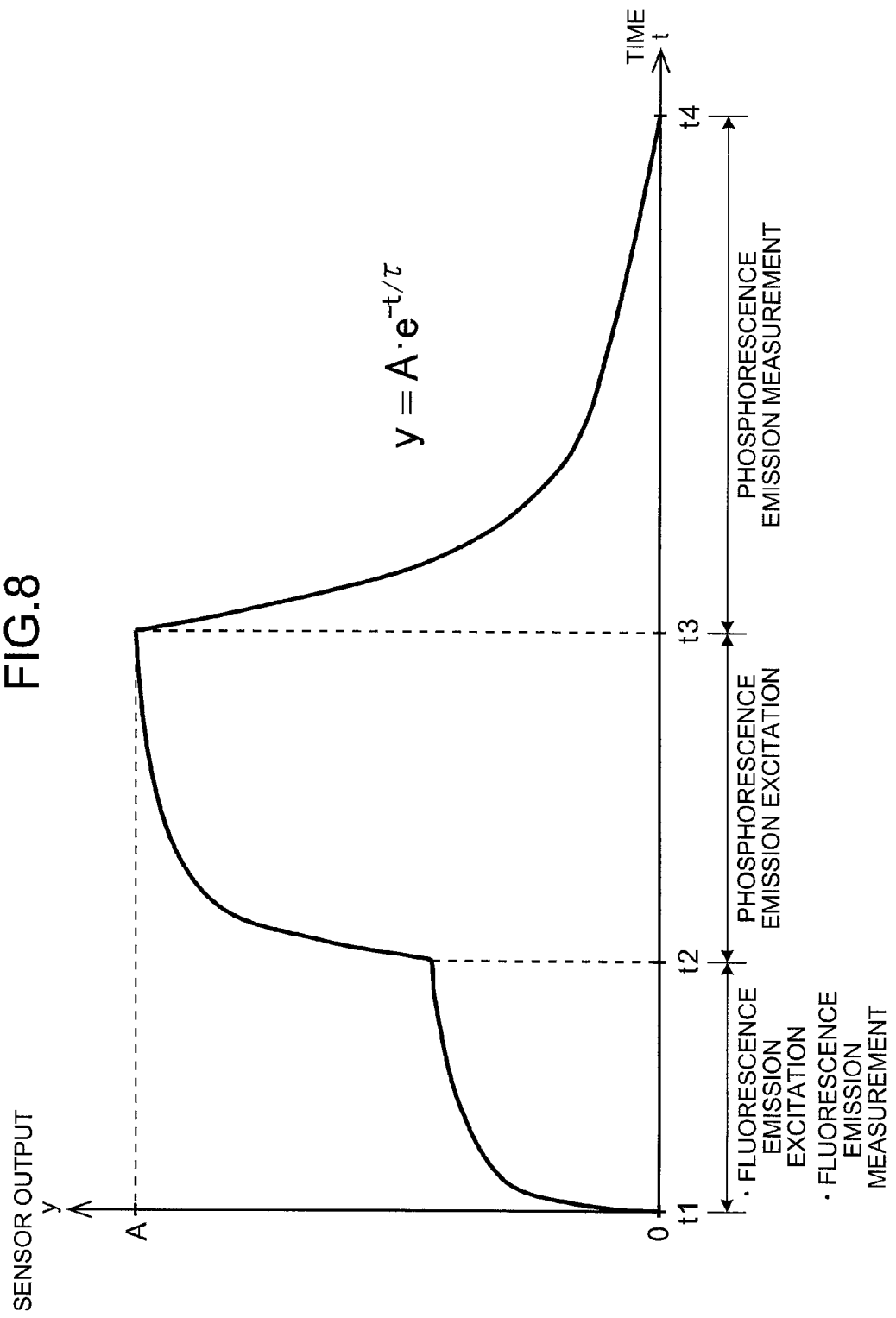
FIG. 8 shows an example of waveforms of signals that are outputted from the fluorescence and phosphorescence sensor upon measuring the phosphorescence emission.

FIG. 8 shows an example of a time-series waveform of a signal outputted from the fluorescence and phosphorescence sensor 10 upon measuring the phosphorescence emission. When the excitation light is emitted from the light source 15 between the time points t1 and t2, the emission intensity gradually increases because of the fluorescence emission and the phosphorescence emission, and along with this, as shown in FIG. 8, the signal strength obtained by measuring the light emission also gradually increases. The measurement to detect the light emission is performed between those time points t1 and t2. Subsequently, between the time points t2 and t3, to excite the phosphorescence emission, an excitation light that has a higher light quantity than the light quantity of the excitation light emitted between the time points t1 and t2 is emitted from the light source 15. Accordingly, even between the time points t2 and t3, the intensity of the phosphorescence emission gradually increases, and along with this, the signal strength obtained by measuring the emission also gradually increases. Subsequently, when the light source 15 is turned off at the time point t3, the phosphorescence emission changes to the gradually attenuating afterglow, and finally disappears at the time point t4. Along with this, the signal strength obtained by measuring the afterglow also gradually decreases from the time point t3 and disappears at the time point t4.

In the fluorescence and phosphorescence detection device 1, the characteristic of the attenuation curve of the signal obtained by measuring the afterglow between the time points t3 and t4 is acquired as an attenuation characteristic. Specifically, as shown in FIG. 8, time constant "$\tau$" is calculated by approximating the attenuation curve with an exponential function $y=A\times\exp(-t/\tau)$, where "y" represents the output value of the signal outputted from the fluorescence and phosphorescence sensor 10, in other words, the output value of the signal from the fourth photodetection element 14 between the time points t3 and t4, and "t" represents time. The calculated time constant $\tau$ is used as a feature amount indicating the attenuation characteristic of the afterglow. Here, "A" represents an initial value, i.e., a sensor output when the light source 15 is off.

Otherwise, when approximating the attenuation curve with the exponential function gives a heavy load on a microprocessor, an inclination of the curve using plural points from which a feature is obtained may be used as a feature amount. For example, after the light source 15 is off, three sampling values are obtained by sampling three times at intervals of 50 uS. The inclination may be obtained by using any two sampling values from three sampling points.

In this manner, it is possible to determine the genuiness of the banknote 100 by using the time constant $\tau$ calculated by approximating the exponential function or the inclination of the attenuation curve as the feature amount indicating the characteristic of the attenuation curve obtained by measuring the afterglow. For example, when a counterfeit banknote is created by elaborately imitating the genuine banknote 100 having the security mark in which the fluorescence emission and the phosphorescence emission can be excited, if even the security mark is imitated, the fluorescence emission and the phosphorescence emission will be excited on the counterfeit banknote. In the counterfeit banknote 100, the fluorescence emission of a predetermined wavelength band will be excited when the counterfeit banknote 100 is irradiated with the excitation light of a predetermined wavelength band, and if the counterfeit banknote has been imitated such that the afterglow is observed because of the phosphorescence emission of the predetermined wavelength even after the irradiation of the excitation light is stopped, it may not be possible to determine the counterfeit banknote only by visual check with one's eyes. Moreover, when the emission quantity of the fluorescence emission and the emission quantity of the phosphorescence emission in such a counterfeit banknote are almost the same as those for a genuine banknote, even if an emission quantity is measured mechanically, it may not be possible to accurately determine the authenticity of the counterfeit banknote. However, it is difficult to imitate an attenuation curve until the afterglow disappears. Accordingly, in the fluorescence and phosphorescence detection device 1, by using the feature amount based on the attenuation curve, a counterfeit banknote can be detected with high precision.

In the present embodiment, a case is explained as one example in which an ultraviolet light is used as the excitation light to excite the fluorescence emission in the wavelength between 500 nm and 550 nm and to excite the phosphorescence emission in the wavelength above 600 nm; however, the wavelength band of the excitation light can be set based on the wavelength necessary to excite the emission from the banknote 100. Moreover, the wavelength band to be cut by the first to fourth photodetection filters 51 to 54 can be set based on the wavelength band of the light emission to be excited on the banknote 100.

In the present embodiment, an example is explained in which the fluorescence and phosphorescence sensor 10 has four photodetection elements arranged in a matrix of two rows and two columns, and four photodetection filters each of which is arranged corresponding to each photodetection element; however, the number of the photodetection elements and the arrangement thereof are set based on the size of the excited light emission region on the banknote 100 that needs to be measured, the type of the excited light emission, the wavelength band of the excited light emission, and the like.

Moreover, with respect to the method for authenticating the banknote 100 based on the measurement result of the fluorescence emission and the phosphorescence emission, any one or both of the following methods can be used. The first method involves comparing each measurement value obtained in the first to fourth photodetection elements 11 to 14 with a reference value previously stored in the memory unit 40 as the recognition data 42 based on the kind of banknote. The second method involves comparing the feature amount calculated from the attenuation curve of the afterglow with a reference value previously stored in the memory unit 40 as the recognition data 42 based on the kind and the direction of a transportation of a banknote. Moreover, each of the two methods is not limited to the one that uses the measurement result obtained in one measurement for the excited light emission region 110 on the banknote 100. For example, to obtain the measurement result, the measurement may be performed a plurality of times while the excited light emission region 110 passes the measurement region of the fluorescence and phosphorescence sensor 10, and the measured values obtained by performing the measurement a plurality of times may be normalized.

Moreover, an example is explained in FIGS. 7A to 7E and FIG. 8 in which the measurement of the afterglow is started as soon as the light source 15 is turned off at the time point t3; however, the present embodiment is not limited to this method. Specifically, the measurement of the afterglow can be started after a time gap of several tens of microseconds from the turning off of the light source 15 at the time point t3. Between the time points t2 and t3, although the signal outputs from the first to fourth photodetection elements 11 to 14 are not used, each photodetection element continues to receive light. Because the light intensity of the light source 15 is large between the time points t2 and t3, the outputs of the light receiving elements or amplifiers for them would be saturated. Therefore, by securing the time gap before the measurement, the electric charge of the light receiving element can be discharged, and the afterglow can be measured more accurately. For example, when the measurement time for one measurement is 500 μs, the measurement is started after several tens of microseconds after turning off the light source 15.

As explained above, according to the present embodiment, based on the emission measurement condition 41, a lighting timing and a non-lighting timing of the light source 15 is controlled to emit a predetermined excitation light onto the excited light emission region 110 on the banknote 100, and a measurement timing is controlled to measure the light from the excited light emission region 110 that passes through the first to fourth photodetection filters 51 to 54 by using the first to fourth photodetection elements 11 to 14. Accordingly, the fluorescence emission and the phosphorescence emission of each wavelength band corresponding to the respective first to fourth photodetection filters 51 to 54 can be measured with high precision.

Moreover, when the phosphorescence emission has been detected, a feature amount can be acquired form the attenuation curve obtained by measuring the afterglow. Therefore, not only the presence/absence of the phosphorescence emission can be detected, but also it is possible to determine whether the detected phosphorescence emission corresponds to the emission from an authentic paper sheet.

As explained above, the fluorescence and phosphorescence detection device, the fluorescence and phosphorescence detection method, and the paper-sheet processing device equipped with the fluorescence and phosphorescence detection device according to the present invention are useful in detecting with high precision the fluorescence emission and the phosphorescence emission excited on a paper sheet in a plurality of the wavelength bands, and recognizing the paper sheet based on the obtained detection result.

What is claimed is:

1. A fluorescence and phosphorescence detection device comprising:
   a fluorescence and phosphorescence sensor including
      a light source that emits an excitation light of a predetermined wavelength on a paper sheet, and
      a photodetection element that detects fluorescence emission and phosphorescence emission excited on the paper sheet by the excitation light;
   a light-source control unit that controls a light quantity of the light source;
   a data acquiring unit that acquires a time-series waveform of a signal outputted from the fluorescence and phosphorescence sensor in response to detection of the emission in the photodetection element; and
   an emission detecting unit that detects the fluorescence emission from the time-series waveform acquired while the excitation light is emitted from the light source and detects the phosphorescence emission from an attenuation curve appearing on the time-series waveform acquired after the excitation light is turned off, wherein
   the data acquiring unit changes an amplification factor of the signal outputted from the fluorescence and phosphorescence sensor depending on whether the fluorescence emission is to be detected on the paper sheet or the phosphorescence emission is to be detected on the paper sheet, and/or
   the light-source control unit changes the light quantity of the excitation light emitted from the light source depending on whether the fluorescence emission is to be detected on the paper sheet or the phosphorescence emission is to be detected on the paper sheet.

2. The fluorescence and phosphorescence detection device according to claim 1 wherein
   the fluorescence and phosphorescence sensor includes a plurality of the photodetection elements each of which detects an emission of a different wavelength band,
   the data acquiring unit acquires the time-series waveform for each photodetection element, and
   the emission detecting unit detects for each photodetection element the fluorescence emission and the phosphorescence emission from the time-series waveform corresponding to each photodetection element.

3. The fluorescence and phosphorescence detection device according to claim 2 wherein
   the fluorescence and phosphorescence sensor includes a plurality of photodetection filters, each photodetection filter being arranged corresponding to each photodetection element, and
   only light of a predetermined wavelength band corresponding to each photodetection filter passes through each photodetection filter.

4. The fluorescence and phosphorescence detection device according to claim 1, wherein
   the amplification factor of the signal outputted from the fluorescence and phosphorescence sensor when the signal is acquired for a fluorescence emission detection is lower than
   the amplification factor of the signal outputted from the fluorescence and phosphorescence sensor when the signal is acquired for a phosphorescence emission detection.

5. The fluorescence and phosphorescence detection device according to claim 4, wherein
   the data acquiring unit includes one amplifier circuit for the fluorescence emission and the other amplifier circuit for the phosphorescence emission separately.

6. The fluorescence and phosphorescence detection device according to claim 4, wherein
   the data acquiring unit includes one amplifier circuit, and
   the data acquiring unit changes the amplification factor of the amplifier circuit depending on whether the signal is acquired for the fluorescence emission detection or the phosphorescence emission detection.

7. The fluorescence and phosphorescence detection device according to claim 1, the light quantity of the excitation light to detect the fluorescence emission on the paper sheet is lower than
   the light quantity of the excitation light to detect the phosphorescence emission on the paper sheet.

8. The fluorescence and phosphorescence detection device according to claim 7, wherein
   the light-source control unit controls the light source such that, while performing one measurement in a region on the paper sheet, the light source emits the excitation light of a light quantity required to excite the fluorescence emission and the excitation light of a light quantity required to excite the phosphorescence emission.

9. The fluorescence and phosphorescence detection device according to claim 8, wherein the light-source control unit controls a light quantity of the excitation light for exciting the phosphorescence emission based on
  a signal outputted from the fluorescence and phosphorescence sensor upon measuring the fluorescence emission excited by the excitation light, and
  a signal outputted from the fluorescence and phosphorescence sensor upon measuring the phosphorescence emission in a region in which the fluorescence emission was excited.

10. The fluorescence and phosphorescence detection device according to claim 1, wherein
  an inclination of the attenuation curve is used as a feature amount of the attenuation curve.

11. The fluorescence and phosphorescence detection device according to claim 1, wherein
  a time constant obtained by approximating the attenuation curve with an exponential function is used as a feature amount of the attenuation curve.

12. A paper-sheet processing device including the fluorescence and phosphorescence detection device according to claim 1.

13. A fluorescence and phosphorescence detection method comprising:
  acquiring a time-series waveform of a signal outputted from a fluorescence and phosphorescence sensor in response to detection of emission excited on a paper sheet, the fluorescence and phosphorescence sensor including
    a light source that emits an excitation light of a predetermined wavelength on the paper sheet, and
    a photodetection element that detects fluorescence emission and phosphorescence emission excited on the paper sheet by the excitation light;
  detecting by using an emission detecting unit the fluorescence emission from the time-series waveform acquired while the excitation light is emitted from the light source; and
  detecting by using the emission detecting unit the phosphorescence emission from an attenuation curve appearing on the time-series waveform acquired after the excitation light is turned off,
wherein
the fluorescence and phosphorescence detection method further comprising
amplifying the signal outputted from the fluorescence and phosphorescence sensor depending on whether the fluorescence emission is to be detected on the paper sheet or the phosphorescence emission is to be detected on the paper sheet, and/or
controlling a light quantity of the excitation light emitted from the light source depending on whether the fluorescence emission is to be detected on the paper sheet or the phosphorescence emission is to be detected on the paper sheet.

* * * * *